United States Patent [19]
Ruvio

[11] Patent Number: 5,147,301
[45] Date of Patent: Sep. 15, 1992

[54] FEMALE INCONTINENT DEVICE

[76] Inventor: Francesco Ruvio, 1922 E. 28th St., Brooklyn, N.Y. 11229

[21] Appl. No.: 805,039

[22] Filed: Dec. 11, 1991

[51] Int. Cl.⁵ ............................................... A61F 5/44
[52] U.S. Cl. ..................................... 604/98; 604/329; 600/29
[58] Field of Search ............... 600/29.31; 604/96-99, 604/327-331

[56] References Cited

U.S. PATENT DOCUMENTS

| | | | |
|---|---|---|---|
| 388,510 | 8/1888 | Terrell | 604/96 X |
| 4,563,183 | 1/1986 | Barrodale et al. | 604/329 |
| 4,846,819 | 7/1989 | Welch | 604/329 |
| 4,889,533 | 12/1989 | Beecher | 604/330 |
| 4,904,248 | 2/1990 | Vaillancourt | 604/327 X |
| 5,041,077 | 8/1991 | Kulick | 600/29 |

FOREIGN PATENT DOCUMENTS

| | | | |
|---|---|---|---|
| 3800744 | 5/1989 | Fed. Rep. of Germany | 604/99 |
| 2090144 | 7/1982 | United Kingdom | 604/331 |
| 2126902 | 4/1984 | United Kingdom | 604/330 |
| 2127295 | 4/1984 | United Kingdom | 604/96 |

Primary Examiner—Randall L. Green
Assistant Examiner—Mary Beth O. Jones
Attorney, Agent, or Firm—Michael I. Kroll

[57] ABSTRACT

A female incontinent device is provided which consists of a cylindrical stem insertable into a vaginal canal of a patient. An inflatable balloon attached to the stem retains the stem within the vaginal canal of the patient in a stationary position. A structure is connected to the stem for draining urine from the urethral meatus of the patient.

10 Claims, 2 Drawing Sheets

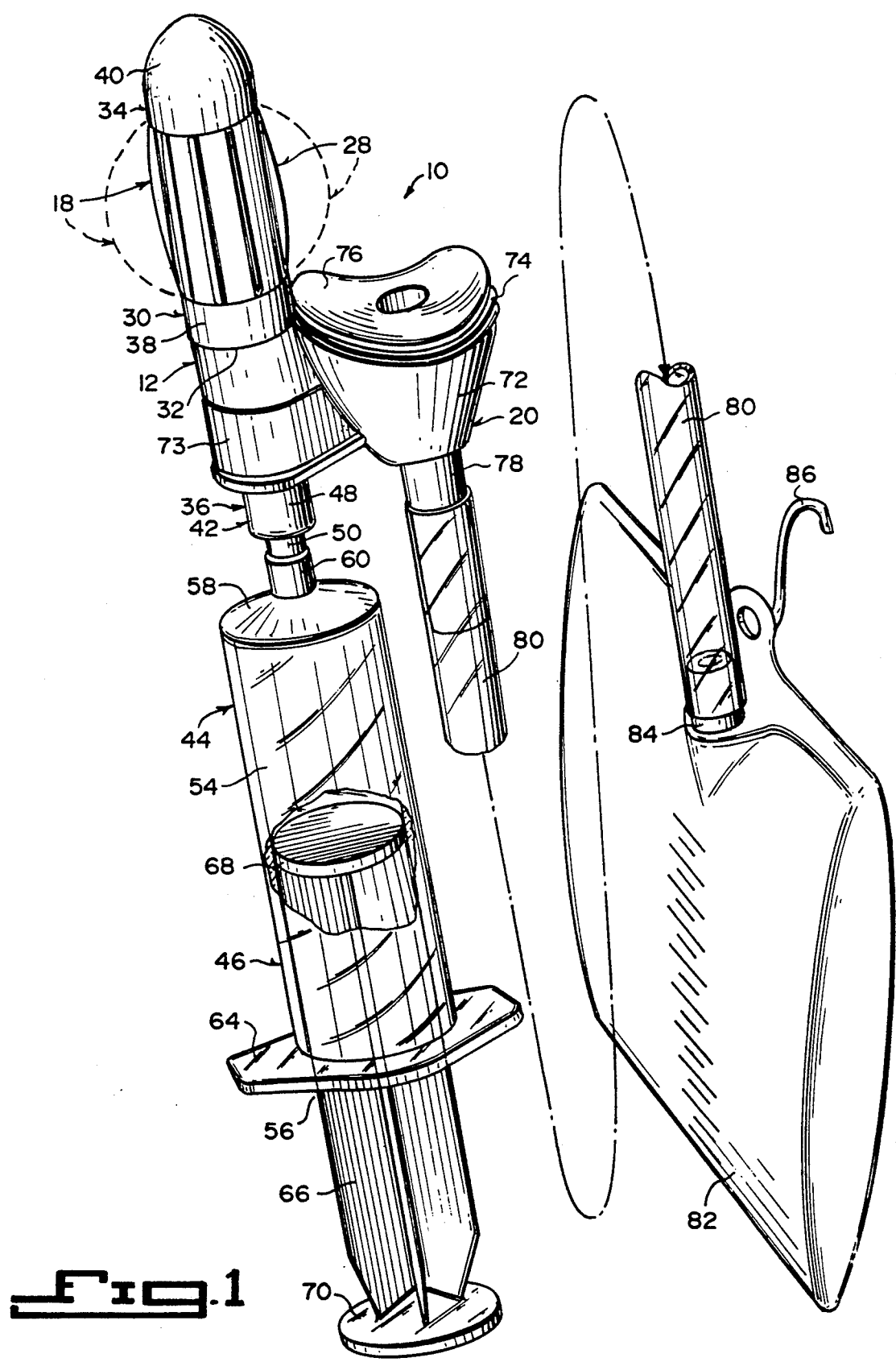

U.S. Patent  Sep. 15, 1992  Sheet 2 of 2  5,147,301
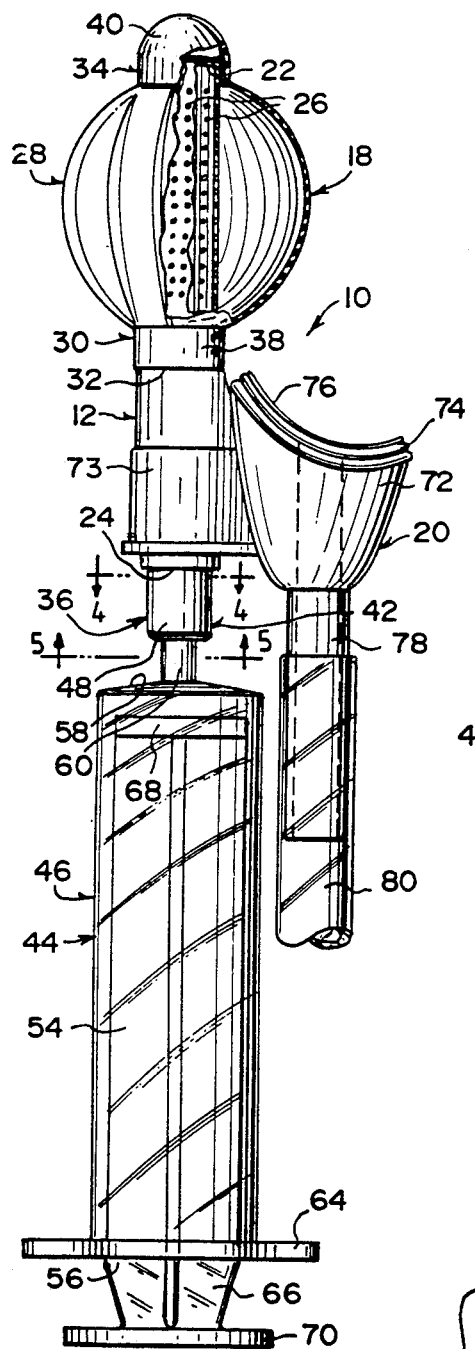
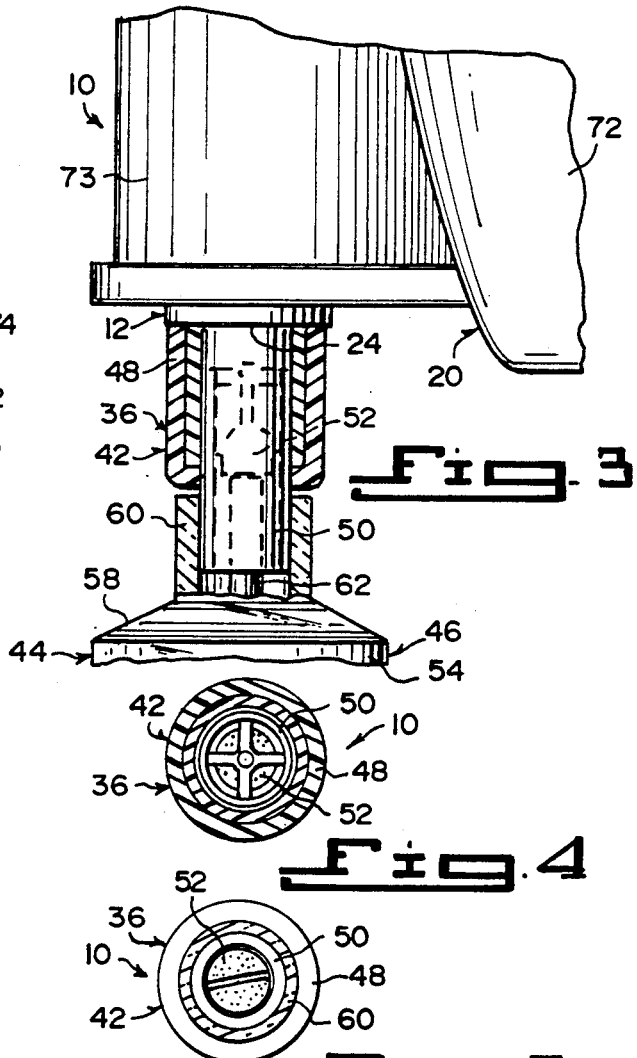
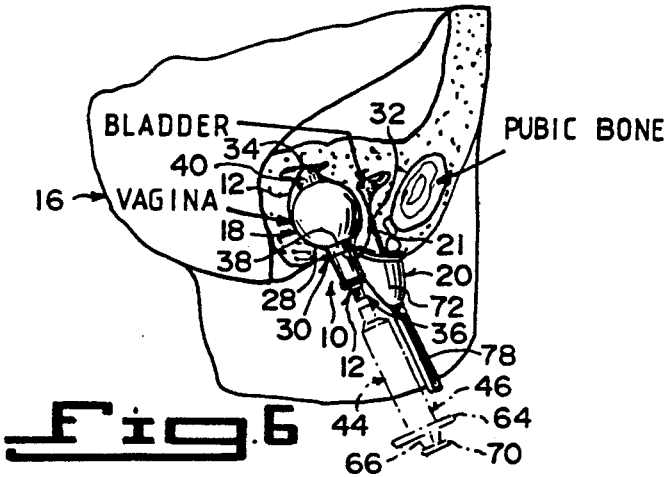

5,147,301

1

FEMALE INCONTINENT DEVICE

BACKGROUND OF THE INVENTION

1. Field of the Invention

The instant invention relates generally to medical tools and more specifically it relates to a female incontinent device.

2. Description of the Prior Art

Numerous medical tools have been provided in prior art that are adapted to include female hygiene equipment, such as a foley catheter which when inserted into the urethral canal for emptying the bladder may in some cases cause a urinary tract infection. While these units may be suitable for the particular purpose to which they address, they would not be as suitable for the purposes of the present invention as heretofore described.

SUMMARY OF THE INVENTION

A primary object of the present invention is to provide a female incontinent device that will overcome the shortcomings of the prior art devices.

Another object is to provide a female incontinent device that is inserted into the vaginal canal and held in place by a balloon anchor, so that a leak proof cup can be retained against the urethral meatus for drainage of urine therefrom.

An additional object is to provide a female incontinent device that is clean, dry and comfortable for a patient, which will prevent decubitus ulcers from forming when being used.

A further object is to provide a female incontinent device that is simple and easy to use.

A still further object is to provide a female incontinent device that is economical in cost to manufacture.

Further objects of the invention will appear as the description proceeds.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

FIG. 1 is a perspective view of the instant invention with parts broken away plugged into a urinary drainage bag.

FIG. 2 is a side elevational view of the instant invention with parts broken away.

FIG. 3 is an enlarged elevational view with parts broken away and in section showing the pump hub in engagement with the valve.

FIG. 4 is a cross sectional view taken along line 4—4 in FIG. 1.

FIG. 5 is a cross sectional view taken along line 5—5 in FIG. 1.

FIG. 6 is a diagrammatic view with parts broken away and in section showing the instant invention installed on a female body, ready for use with the pump in phantom removed therefrom.

DETAILED DESCRIPTION OF THE PREFERRED EMBODIMENTS

Turning now descriptively to the drawings, in which similar reference characters denote similar elements throughout the several views, the Figures illustrate a female incontinent device 10 which consists of a cylindrical stem 12 insertable into a vaginal canal 14 of a patient 16. A mechanism 18 is for retaining the stem 12 within the vaginal canal 14 of the patient 16 in a stationary position. A structure 20 is connected to the stem 12 for draining urine from the urethral meatus 21 of the patient 16.

The retaining mechanism 18 includes the stem 12 having a closed end 22, an open end 24 and a plurality of small orifices or slits 26 located near the closed end 22 thereof. A balloon anchor 28 is placed over the closed end 22 and the orifices or slits 26 of the stem 12. A retainer 30 is for securing a mouth 32 of the balloon anchor 28 to the stem 12. A cap 34 fits onto the balloon anchor 28 holding the stem 12 and the balloon anchor 28 stationary at the closed end 22 of the stem 12. An apparatus 36 is at the open end 24 of the stem 12 for controlling the flow of fluid or air into the stem 12 for inflating the balloon anchor 28, so as to retain the stem 12 within the vaginal canal 14 and for deflating the balloon anchor 28, so that the stem 12 can be removed from the vaginal canal 14 when needed.

The retainer 30 is an elastic band 38 which fits about the mouth 32 of the balloon anchor 28. The cap 34 is dome shaped at 40, so that the stem 12 can be easily inserted within the vaginal canal 14 of the patient 16. The fluid or air flow controlling mechanism 36 is a valve assembly 42 mounted to the open end 24 of the stem 12.

The female incontinent device 10 further includes a mechanism 44 for actuating the valve assembly 42 and forcing the fluid or air through the stem 12 and into the balloon anchor 28 for inflating the balloon anchor 28 after the stem 12 is inserted into the vaginal canal 14. The actuating mechanism 44 is a hand held pump 46, which is engagable with the valve assembly 42.

The valve assembly 42 includes a housing 48 attached to the open end 24 of the stem 12, a sleeve 50 depending from the housing 48 and a valve member 52 carried within the sleeve 50. The pump 46 includes a barrel 54 having an open end 56 and a generally closed end 58. A hub 60 is mounted onto the generally closed end 58 of the barrel 54. The hub 60 is sized to fit over the sleeve 50 on the valve assembly 42. A hollow pin 62 extends upwardly from the generally closed end 58 of the barrel 54 within the hub 60, so as to engage the valve member 52 when the hub 60 fits over the sleeve 50 on the valve assembly 42. A finger flange 64 is at the open end 56 of the barrel 54. A plunger 66 slideably fits into the open end 56 of the barrel 54. A stopper 68 is on the inner end of the plunger 66 within the barrel 54, and a thumb rest 70 is on the outer end of the plunger 66. When the plunger 66 is depressed the fluid or air will be forced through the hollow pin 62, past the valve member 52, into the stem 12 and out through the orifices or slits 26 to inflate the balloon anchor 28. To deflate the balloon, the hollow pin 62 engages the bottom surface of valve member 52 to lift it from its valve seat, allowing the fluid or air to be removed from the balloon.

The draining structure 20 includes an anatomically shaped urine collecting cup 72 that is affixed onto the stem 12 or is part of the stem 12 at 73 near the open end 24 of the stem 12. A gasket 74 is mounted to the top of the cup 72 to form a leak proof seal when the cup is placed against the urethral meatus 21 of the patient 16. A shield 76 is attached onto the gasket 74 to prevent back flow of the urine. A drainage conduit 78 depends from the cup 72, so as to remove the urine from the cup 72.

The draining structure 20 further includes an elongated flexible tube 80 connected at one end to the drainage conduit 78. A urinary drainage bag 82 has a neck 84 connected to another end of the elongated flexible tube 80. A hook 86 is for hanging the urinary drainage bag 82 at a point below the cup 72 to receive and retain the urine from the cup 72.

LIST OF REFERENCE NUMBERS 10 female incontinent device
12 cylindrical stem
14 vaginal canal
16 patient
18 retaining mechanism
20 draining structure
21 urethral meatus
22 closed end of 12
24 open end of 12
26 small orifice or slit in 12
28 balloon anchor
30 retainer
32 mouth of 28
34 cap
36 fluid or air flow controlling apparatus
38 elastic band for 30
40 dome shaped for 34
42 valve assembly for 36
44 actuating mechanism
46 hand held pump
48 housing
50 sleeve
52 valve member
54 barrel
56 open end of 54
58 generally closed end of 54
60 hub
62 hollow pin
64 finger flange on 54
66 plunger
68 stopper on 66
70 thumb rest on 66
72 urine collecting cup
74 gasket
76 shield
78 drainage conduit
80 elongated flexible tube
82 urinary drainage bag
84 neck on 82
86 hook It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. A female incontinent device which comprises:
    a) a cylindrical stem insertable into a vaginal canal of a patient;
    b) means for retaining said stem within the vaginal canal of the patient in a stationary position;
    c) means rigidly connected to said stem for draining urine from the urethral meatus of the patient;
    d) wherein said stem has a closed end, an open end and a plurality of small orifices located near the closed end thereof;
    e) and wherein said retaining means includes:
        a balloon anchor placed over the closed end and the orifices of said stem;
        a retainer for securing a mouth of said balloon anchor to said stem;
        a cap to fit onto said balloon anchor for holding said stem and said balloon anchor stationary at the closed end of said stem; and
        means at the open end of said stem for controlling the flow of fluid/air into said stem for inflating said balloon anchor, so as to retain said stem within the vaginal canal and for deflating said balloon anchor, so that said stem can be removed from the vaginal canal when needed.

2. A female incontinent device as recited in claim 6, wherein said retainer is an elastic band which fits about the mouth of said balloon anchor.

3. A female incontinent device as recited in claim 2, wherein said cap is dome shaped so that said stem can be easily inserted within the vaginal canal of the patient.

4. A female incontinent device as recited in claim 3, wherein said fluid/air flow controlling means is a valve assembly mounted to the open end of said stem.

5. A female incontinent device as recited in claim 4, further including means for actuating said valve assembly and forcing the fluid/air through said stem and into said balloon anchor for inflating said balloon anchor after said stem is inserted into the vaginal canal.

6. A female incontinent device as recited in claim 5, wherein said actuating means includes a hand held pump engagable with said valve assembly.

7. A female incontinent device as recited in claim 6, wherein said valve assembly includes:
    a) a housing attached to the open end of said stem;
    b) a sleeve depending from said housing; and
    c) a valve member carried within said sleeve.

8. A female incontinent device as recited in claim 7, wherein said pump includes:
    a) a barrel having an open end and a generally closed end;
    b) a hub mounted onto the generally closed end of said barrel, said hub sized to fit over said sleeve on said valve assembly;
    c) a hollow pin extending upwardly from the generally closed end of said barrel within said hub, so as to engage with and open said valve member when said hub fits over said sleeve on said valve assembly;
    d) a finger flange at the open end of said barrel;
    e)1 a plunger which slideably fits into the open end of said barrel;

f) a stopper on the inner end of said plunger within said barrel; and g) a thumb rest on the outer end of said plunger, so that when said plunger is depressed the fluid/air will be forced through said hollow pin, past said valve member, into said stem and out through the orifices to inflate said balloon anchor.

9. A female incontinent device as recited in claim 8, wherein said draining means includes:

a) an anatomically shaped urine collecting cup disposed at said stem near the open end of said stem;

b) a gasket mounted to the top of said cup to form a leak proof seal when said cup is placed against the urethral meatus of the patient;

c) a shield attached onto said gasket to prevent back flow of the urine; and d) a drainage conduit depending from said cup, so as to remove the urine from said cup.

10. A female incontinent device as recited in claim 9, wherein said draining means further includes:

a) an elongated flexible tube connected at one end to said drainage conduit;

b) a urinary drainage bag having a neck connected to another end of said elongated flexible tube; and c) a hook for hanging said urinary drainage bag at a point below said cup to receive and retain the urine from said cup.

* * * * *